United States Patent [19]
Tieman et al.

[11] 3,971,774
[45] July 27, 1976

[54] 2-(NITROMETHYLENE)-1,3-DIAZEPINES

[75] Inventors: Charles H. Tieman; Willy D. Kollmeyer; Steven A. Roman, all of Modesto, Calif.

[73] Assignee: Shell Oil Company, Houston, Tex.

[22] Filed: Nov. 7, 1975

[21] Appl. No.: 630,065

Related U.S. Application Data

[60] Division of Ser. No. 510,100, Sept. 27, 1974, which is a continuation-in-part of Ser. No. 412,373, Nov. 1, 1973, abandoned.

[52] U.S. Cl. ........................ 260/239 BC; 260/309.6; 260/251 R; 260/256.4 H; 260/256.5 R; 424/244; 424/251; 424/273

[51] Int. Cl.² .................................... C07D 239/02
[58] Field of Search ............................ 260/239 BC

[56]  References Cited
UNITED STATES PATENTS

| | | | |
|---|---|---|---|
| 3,332,948 | 7/1967 | Blatter | 260/251 |
| 3,502,671 | 3/1970 | Hodge | 260/251 |

*Primary Examiner*—Lewis Gotts
*Assistant Examiner*—Dolph H. Torrence

[57] ABSTRACT

Novel insecticidal 2-(nitromethylene)-1,3-diazacycloalkanes.

1 Claim, No Drawings

2-(NITROMETHYLENE)-1,3-DIAZEPINES

This application is a division of copending application Ser. No. 510,100, filed Sept. 27, 1974, which was a continuation-in-part of application Ser. No. 412,373, filed Nov. 1, 1973, now abandoned.

DESCRIPTION OF THE INVENTION

It has been found that useful insecticidal activity is possessed by certain 2-(nitromethylene)-1,3-diazacycloalkanes. These compounds have been found to be resonance hybrids, the principal forms contributing thereto being described by the formulae:

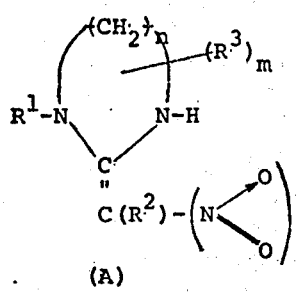

(A)

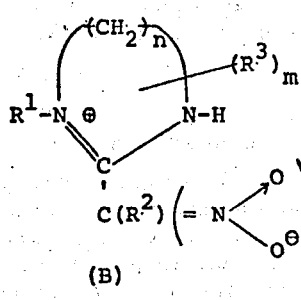

(B)

(wherein the symbols have the respective meanings set out hereinafter), which also can exist in two tautomeric forms: one form being the resonance hybrid described above and the other being described by the formula:

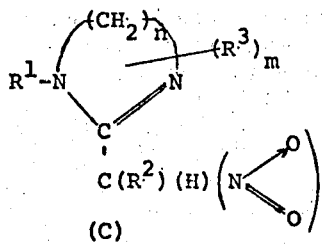

(C)

This form (C) can be designated as a 2-(nitromethyl)-1,3-diaza-2-cycloalkene. The left-hand form (A) can be designated as a 2-(nitromethylene)-1,3-diazacycloalkane, while the right-hand form (B) can be designated as a 2-(aci-nitromethyl)-1,3-diazacycloalkanonium hydroxide inner salt.

The resonance hybrid may exist as either of two geometric isomers, depending upon the spatial relationship of the moieties about the bond between the carbon atom of the nitromethylene moiety and the ring carbon atom to which it is joined.

In this specification, for the sake of simplicity, these compounds will be referred to generally as 2-(nitromethylene)-1,3-diazacycloalkanes. This term is intended to include all of the contributors to the resonance hybrid, the geometric isomers, and the tautomers, as well as mixtures thereof.

In these compounds, the respective symbols have the following meanings: $n$ is two, three or four; when $n$ is two or three, $R^1$ is straight-chain alkyl, haloalkyl, alkenyl, haloalkenyl, alkynyl, or amino; $R^2$ is hydrogen, middle halogen (i.e., Cl or Br) or phenylthio, optionally substituted by one or more of middle halogen, nitro or alkyl or alkoxy of from one to three carbon atoms; $R^3$ is alkyl, and $m$ is zero or one; when $n$ is four; $R^1$ is alkyl or alkenyl, $R^2$ is hydrogen and $m$ is zero.

The invention also includes derivatives of the tautomeric form (C) wherein the alpha-hydrogen is replaced — for example, by halogen, particularly middle halogen.

In all cases, each alkyl, alkenyl, alkynyl or alkylene moiety contains no more than eight, or preferably no more than six, carbon atoms; each may, unless otherwise expressly indicated, be of straight-chain or branched-chain configuration.

Of particular interest is the sub-class of this genus of compounds wherein $n = 2$ or 3, $R^1$ is $C_{1-3}$ alkyl, alkenyl, haloalkenyl or alkynyl, $R^2$ is hydrogen or middle halogen (Cl or Br) and $m = 0$. Of these, highest activity has been associated with the compounds wherein $n = 2$ or 3, $R^1$ is methyl, ethyl, 2-propenyl, 3-chloro-2-propenyl, or 2-propynyl, and $R^2$ is hydrogen, phenylthio or 4-methoxyphenylthio.

Compounds of the invention can be prepared by five procedures:

Method A — treating a nitroketene dimethyl mercaptole (NKDM) with a diamine, including suitably substituted diamines (referring to the definition of $R^1$ and $R^3$); R. Gompper and H. Schaefer, Berichte, 100, 591 (1967);

Method B — substituting a moiety on the <NH function of a 2-(nitromethylene)-1,3-diazacycloalkane (NMDCA); a method for preparing the latter kind of compound is disclosed in Gompper and Schaefer, supra;

Method C — reaction of trichloronitroethylene (TCNE) (G. B. Bachmann, et al, J. Org. Chem. 25, 1312 (1960); U.S. Pat. No. 3,054,828) with a diamine including suitably substituted diamines.

Method D — direct halogenation of compounds prepared by any of the above methods.

Method E — Compounds of this invention wherein $R^2$ is an optionally substituted phenylthio moiety can be prepared by reacting the precursor wherein $R^2$ is hydrogen with the appropriate phenylsulfenyl chloride or bromide in the presence of an acid acceptor.

In Method A, the reaction is carried out by mixing the reactants in a suitable solvent at a moderately elevated temperature under anhydrous conditions. Suitably, the reaction can be carried out at from about 50° to about 100°C. Often it may be convenient to conduct the reaction at the reflux temperature. Suitable solvents are the lower alkanols, particularly ethanol or isopropyl alcohol. In some cases it will be found desirable to employ a slight (5–10%) to moderate (50–75%) excess of the diamine reactant. The unsubstituted and appropriately substituted diamines are generally known materials.

In Method B, the N-substitution is conveniently effected by introducing the diazacycloalkane (NMDCA), which may be prepared by Method A, into a cold anhydrous mixture of a dispersion of sodium hydride in oil and dimethylformamide as solvent in an inert atmosphere and then treating the resulting mixture (containing the N-sodium derivative of the NMDCA) with a halide of the moiety to be substituted; the reaction is general for alkylating agents. Suitably, addition of the halide is conducted at a temperature below about 10°C and is conveniently conducted at icebath temperature. It will be found desirable in many cases to employ a slight (5–25%) excess of the sodium hydride, and a slight (5–10%) to moderate (50–75%) excess of the halide.

In Method C, the TCNE is introduced into a stirred mixture of the diamine and sodium carbonate in a suitable solvent, at a temperature below about 15°C, then the reaction mixture is stirred without cooling. Suitable solvents are the lower alkanols, particularly methanol. Suitably, equivalent amounts of TCNE and sodium carbonate are employed, these being in a slight (5–10%) to moderate excess (20–30%) relative to the diamine. The unsubstituted and appropriately substituted diamines are generally known materials.

In Method D, a solution of the heterocyclic compound, optionally containing an acid acceptor, in a suitable solvent (water is ordinarily suitable and convenient) is treated with the halogen to replace the (or both of the) alpha-hydrogen atom(s) on the nitromethylene (or nitromethyl)moiety. The reaction can be conducted at room temperature or somewhat above (for example, 15°–45°C). The number of halogen atoms which are introduced depends upon the character of $R^2$ (only if $R^2 = H$ can two halogens be substituted readily) and in part upon the amount of halogen and/or acid acceptor used — relatively, the more halogen used, the greater the substitution. In some cases, the product is sufficiently non-basic in character that it will not form a salt with the by-product hydrogen halide, even when no acid acceptor is present. In such cases, the desired product can be recovered by extracting the reaction mixture with a suitable non-water soluble solvent, then evaporating the solvent. Suitable solvents are the halogenated alkanes such as methylene chloride. Where the product forms the salt, the product can be recovered by treating the reaction mixture with a base, such as sodium bicarbonate, to spring the product, then recovering it by solvent extraction of the aqueous mixture with a halogenated alkane.

In Method E, a solvent such as methylene chloride preferably is used, and the acid acceptor suitably is a tertiary alkylamine, such as triethylamine, or an aromatic amine such as pyridine. The reaction is conveniently conducted by mixing the reactants at room temperature or somewhat below, and cooling if needed to maintain the temperature of the reaction mixture at or moderately above room temperature. Some of the phenylsulfenyl halides are known compounds. Others are readily prepared by direct halogenation of the appropriate thiol or disulfide, according to the procedure described by E. Kühle, Synthesis 1970, 561–550.

The techniques for recovery and purification of the products from the final crude reaction mixtures are conventional and are illustrated in the examples indicated hereinafter.

These procedures for preparing compounds of this invention are illustrated in the following examples of the preparation of particular species of the compounds of this invention. In all cases, the identity of the product was confirmed by elemental analysis, and by infrared and nuclear magnetic resonance spectrum analyses.

EXAMPLE 1

Method A, 1-methyl-2-(nitromethylene)imidazolidine;

1. A mixture of 16.52 grams of NKDM, 8.14 grams of N-methylethylenediamine and 200 milliliters of absolute ethanol was refluxed for 1.5 hours. The mixture was then cooled, and the reddish brown crystalline product that formed was removed by filtration. The product melting point: 142.5°–143.5°C. A 6.3 gram portion of the product was recrystallized from ethanol (charcoal) to give 4.8 grams of 1, as white needles, melting point: 142.5°–143.5°C.

EXAMPLE 2

Method A,
Hexahydro-1-methyl-2-(nitromethylene)pyrimidine;

2. A mixture of 8.2 grams NKDM, 7.3 grams of N-methyl-1,3-propanediamine and 100 milliliters of absolute ethanol was refluxed for 1 hour. The mixture was then cooled, precipitating 4.9 grams of 2 as tan crystals, melting point: 114°–115°C.

EXAMPLE 3

Method B,
2-(nitromethylene)-1-(2-propynyl)imidazolidine;

3. An ice-cooled mixture of 50 milliliters of dry dimethylformamide and 1.77 grams of a 57% by weight dispersion of sodium hydride in mineral oil, maintained under nitrogen atmosphere, was treated with 5.16 grams of 2-(nitromethylene)imidazolidine. After stirring for 1 hour, 7.97 grams of propargyl bromide was added. The mixture was stirred at 10° for an additional hour, allowed to warm to room temperature, and poured into 400 milliliters of saturated aqueous sodium sulfate. The product was extracted with three 300-milliliter portions of methylene chloride. The combined extract was dried with magnesium sulfate and the solvent was evaporated. Addition of ether to the residual oil gave a solid which was recrystallized from chloroform (charcoal) to give 3.1 grams of 3, as tan crystals, melting point: 146°–147°C.

EXAMPLE 4

Method B,
2-(nitromethylene)-1-(2-propenyl)imidazolidine;

4. To 1.77 grams of a 57% by weight dispersion of sodium hydride in oil in 50 milliliters of dry dimethylformamide was added 5.16 grams of 2-(nitromethylene)imidazolidine. The mixture was cooled with an icebath, stirred and maintained under a nitrogen atmosphere. After 1.5 hours, 5.08 grams of allyl bromide was added. The mixture was stirred at about 10° for an additional hour, then allowed to warm to room temperature and poured into 400 milliliters of saturated aqueous sodium sulfate. The resulting mixture was extracted thrice with 300 milliliter portions of methylene chloride. The combined extract was dried (magnesium sulfate) and the solvent was evaporated. Addition of ether to the residue gave an oily red solid, which on recrystallization from chloroform (charcoal), gave 2.1 grams of 4 as tan crystals, melting point: 97°–98°.

EXAMPLE 5

Method B,
Hexahydro-1-methyl-2-(nitromethylene)-1H-1,3-diazepine;

5. By the procedure of Method A, reaction of NKDM with 1,4-diaminobutane gave hexahydro-2-(nitromethylene)-1H-1,3-diazepine, melting point: 152°–154°. 3.14 grams of this compound in 25 milliliters of dry dimethylformamide was treated with 0.884 gram of a 57% by weight dispersion of sodium hydride in oil and then with 2.98 grams of methyl iodide. Experimental conditions and work-up were like those of Examples 3 and 4. Recrystallization of the crude product from methanol gave 0.6 gram of 5, as a tan solid, melting point: 88°–89°C.

EXAMPLE 6

Method C,
2-(chloronitromethylene)-1-methylimidazolidine;

6. To a cooled (10°–15°) and stirred mixture of 3.6 grams of N-methylethylenediamine and 8.3 grams of potassium carbonate in 50 milliliters of methanol was added slowly 9.1 grams of TCNE. After 1 hour, the mixture was filtered. The solid obtained by evaporation of the filtrate was recrystallized from ethanol to give 1.5 grams of 6, melting point: 145°–6° C with decomposition.

The following other species of the compounds of this invention have been prepared, by the indicated method.

EXAMPLE 7

1-ethyl-2-(nitromethylene)imidazolidine;

7. Method A, reacting NKDM with N-ethylethylenediamine. Melting point: 110°–111°C.

EXAMPLE 8

2-(nitromethylene)-1-propylimidazolidine

8. Method A, reacting NKDM with N-propylethylenediamine, Melting point: 147°–148°C.

EXAMPLE 9

1,4-dimethyl-2-(nitromethylene)- and 1,5-dimethyl-2-(nitromethylene)imidazolidine, 4/1 mixture of isomers;

9. Method B, reacting 4-methyl-2-(nitromethylene)imidazoline with methyl iodide: Melting point: 100°–102°C.

EXAMPLE 10

Hexahydro-2-(nitromethylene)-1-(2-propenyl)pyrimidine

10. Method B, reacting hexahydro-2-(nitromethylene)pyrimidine (HNMP), prepared by Method A by reaction of NKDM with 1,3-propanediamine, with allyl bromide. Melting point: 125°–126°C.

EXAMPLE 11

Hexahydro-2-(nitromethylene)-1-(2-propynyl)pyrimidine

11. Method B, reacting HNMP with propargyl bromide. Melting point: 157°–158°C.

EXAMPLE 12

1-((E)-3-chloro-2-propenyl)-2-(nitromethylene)imidazolidine

12. Method B, reacting 2-(nitromethylene)imidazolidine with trans-1,3-dichloro-1-propene. Melting point: 134°–135°C.

EXAMPLE 13

(Method B) -
1-(2-chloro-2-propenyl)-2-(nitromethylene)imidazolidine

13. The sodium salt of 2-(nitromethylene)imidazolidine was prepared by treating a mixture of 1.33 grams of a 57% by weight dispersion of sodium hydride in oil and 35 milliliters of dimethylformamide with 3.87 grams of 2-(nitromethylene)imidazolidine. The resulting mixture was cooled to about 20°C and stirred while adding 3.47 grams of 2,3-dichloro-1-propene dropwise. After 2 hours, the mixture was stripped under reduced pressure. The residue was slurried in methylene chloride and filtered. The solvent was evaporated from the filtrate, and the resulting crude solid product was recrystallized from ethanol to give 13, as tan crystals, melting point: 146°–147°C.

EXAMPLE 14

1-amino-2-(nitromethylene)imidazolidine

14. Method A, NKDM being reacted with N-aminoethylene diamine. Melting point: 159°–160°.

EXAMPLE 15

Method D,
2-(bromonitromethylene)-1-methylimidazolidine

15. A stirred solution of 3.57 grams of 1-methyl-2-(nitromethylene)imidazolidine (Compound 1) in 25 milliliters of water was treated dropwise with 3.99 grams of bromine at room temperature. After 30 minutes, the reaction mixture was extracted with methylene chloride. The extract was dried (MgSO$_4$) and the solvent was evaporated to give 3.0 grams of crude product, melting point 100° (with vigorous decomposition). Recrystallization of the crude product from methylene chloride gave 15, melting point: 97° (explodes).

EXAMPLE 16

Method D, 2-(dibromonitromethyl)-1-methyl-1,4,5,6 tetrahydropyrimidine 16. 7.99 grams of bromine was added dropwise to a stirred solution of 7.85 grams of Compound 2 in 50 milliliters of water. After 30 minutes the mixture was treated with 4.2 grams of sodium bicarbonate in 20 milliliters of water. The mixture then was extracted with methylene chloride. The extract was dried (MgSO$_4$) and the solvent was evaporated to give 16, melting point: 106°–107°.

EXAMPLE 17

Method D,
2-(dibromonitromethyl)-4,5-dihydro-1-methyl-1H-imidazole

17. A stirred solution of 7.15 grams of 1 and 5.3 grams of sodium carbonate in 50 milliliters of water was treated at room temperature with 16 grams of 24 and 33 were below 0.5. Compounds 1 and 2 were also tested against the black cutworm and cabbage looper, the respective $LC_{50}$ dosages being in all cases below 0.04. Compounds 1 and 2 also were found to be very toxic to the Egyptian cotton leafworm. In tests on cotton, Compound 1 controlled larvae of the cotton bollworm and tobacco budworm. It also controlled whiteflies.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material, which may be inorganic or organic and of synthetic or natural origin, with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Many of the compounds of this invention which have been prepared have shown substantial solubility in water, so that water will be a suitable carrier in such cases, simplifying formulation of those active compounds. If the water solubility of a particular compound is insufficient, a different solvent can be used. Also, in some cases a liquid in which the toxicant is insoluble or only slightly soluble can be used as carrier.

Examples of such solvents and liquid carriers generally are alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight mono-, di- and trialkylamines; condensates of these with ethylene oxide and/or propylene oxide; condensation products of fatty alcohols or alkyl phenols for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated castor oil, and sodium alkyaryl sulfonats such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of a dispersing agent and, where necessary, up to 10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

What is claimed is:

1. A compound of the group consisting of compounds of the formula:

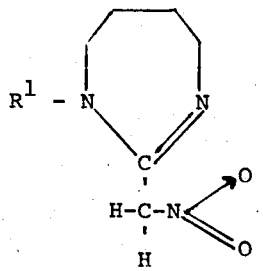

derivatives thereof wherein the alpha hydrogen is replaced by middle halogen and resonance hybrids represented by the formulae:

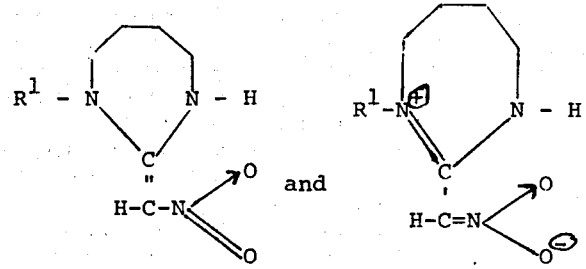

wherein $R^1$ contains up to eight carbon atoms and is alkyl or alkenyl.

* * * * *